US008613843B2

(12) United States Patent
Jones et al.

(10) Patent No.: US 8,613,843 B2
(45) Date of Patent: Dec. 24, 2013

(54) ELECTRO-CHEMICAL SENSOR (75) Inventors: Timothy Gareth John Jones, Cottenham (GB); Li Jiang, Newton, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 917 days.

(21) Appl. No.: 11/628,823

(22) PCT Filed: Jun. 3, 2005

(86) PCT No.: PCT/GB2005/002237
§ 371 (c)(1),
(2), (4) Date: May 12, 2008

(87) PCT Pub. No.: WO2005/121779
PCT Pub. Date: Dec. 22, 2005

(65) Prior Publication Data
US 2009/0014325 A1    Jan. 15, 2009

(30) Foreign Application Priority Data
Jun. 9, 2004   (GB) .................................. 0412926.8

(51) Int. Cl.
*G01N 27/407* (2006.01)

(52) U.S. Cl.
USPC ........... 204/412; 204/415; 204/424; 204/431; 204/432

(58) Field of Classification Search
USPC ............... 204/280, 400–435; 205/775, 782.5, 205/786.5, 787.5, 793, 794.5
See application file for complete search history.

(56) References Cited

U.S. PATENT DOCUMENTS

| 3,305,457 A | 2/1967 | Hyman |
| 3,780,575 A | 12/1973 | Urbanosky |
| 3,859,851 A | 1/1975 | Urbanosky |
| 4,282,487 A | 8/1981 | Warren et al. |
| 4,802,143 A | 1/1989 | Smith |
| 4,911,794 A * | 3/1990 | Parce et al. .................. 205/778 |
| 4,994,671 A | 2/1991 | Safinya et al. |
| 5,173,166 A | 12/1992 | Tomantschger et al. |
| 5,322,611 A | 6/1994 | Zaromb |
| 5,351,532 A | 10/1994 | Hager |
| 5,416,320 A | 5/1995 | North |
| 5,445,228 A | 8/1995 | Rathmell et al. |
| 5,517,024 A | 5/1996 | Mullins et al. |

(Continued)

FOREIGN PATENT DOCUMENTS

| EP | 0 952 447 A1 | 10/1999 |
| GB | 2 391 314 A | 2/2004 |

(Continued)

OTHER PUBLICATIONS

JP59153163A english equivalent of abstract Noda et al. Sep. 1984.*

(Continued)

*Primary Examiner* — Susan D Leong (57) ABSTRACT

An electro-chemical sensor for methane is described having a catalyst to react methane or other low molecular weight hydrocarbons and a detector to detect the turnover or reaction rate and using such information to determine the concentration of the methane or other low molecular weight species. The sensor is preferably used for measurements in a wellbore.

10 Claims, 6 Drawing Sheets

(56) References Cited

U.S. PATENT DOCUMENTS

| | | | |
|---|---|---|---|
| 5,736,650 A | | 4/1998 | Hiron et al. |
| 5,829,520 A | | 11/1998 | Johnson |
| 5,902,556 A | | 5/1999 | van de Vyver et al. |
| 6,023,340 A | | 2/2000 | Wu et al. |
| 6,051,123 A | * | 4/2000 | Joshi et al. ............... 204/424 |
| 6,103,080 A | | 8/2000 | Pham et al. |
| 2002/0061431 A1 | * | 5/2002 | Koyama et al. ............ 429/33 |
| 2003/0089228 A1 | * | 5/2003 | Kulprathipanja et al. ....... 95/45 |
| 2004/0045874 A1 | * | 3/2004 | Olivier-Bourbigou et al. ............... 208/238 |
| 2005/0173245 A1 | * | 8/2005 | Feldman et al. ......... 204/403.01 |
| 2005/0221141 A1 | * | 10/2005 | Hampden-Smith et al. .... 429/33 |
| 2006/0042955 A1 | * | 3/2006 | Villalobos ................. 205/628 |
| 2006/0272775 A1 | * | 12/2006 | Horsky et al. ............ 156/345.37 |

FOREIGN PATENT DOCUMENTS

| | | | |
|---|---|---|---|
| JP | 59153163 A | * | 9/1984 |
| JP | 1-250852 A | | 10/1989 |
| WO | 99/00575 A2 | | 1/1999 |
| WO | 99/00575 A3 | | 1/1999 |
| WO | 2004/011929 A1 | | 2/2004 |

OTHER PUBLICATIONS

Anshits et al $C_2$ hydrocarbons formation from methane on silver membrane Catalysis Today, vol. 6, 1990, pp. 593-600.

Baik et al Mechanistic studies on the hydroxylation of methane by methane monooxygenase Chemical Reviews, vol. 103, 2003, pp. 2385-2419.

Chan et al Toward delineating the structure and function of the particulate methane monooxygenase from methanotrophic bacteria Biochemistry, vol. 43, 2004, pp. 4421-4430.

Fukushima et al Molecular ordering of organic molten salts triggered by single-walled carbon nanotubes Science, vol. 300, Jun. 2003, pp. 2072-2074.

Khenkin et al Biomimetic alkane oxidation in the presence of iron complexes New J. Chem. vol. 13, 1989, pp. 659-667.

Madigan et al Extremophiles Scientific American, Apr. 1997, pp. 82-87.

Nguyen et al The nature of the copper ions in the membranes containing the particulate methane monooxygenase from methylococcus capsulatus (Bath) Biological Chemistry, vol. 269, No. 21, 1994, pp. 14995-15005.

Periana et al A mercury-catalyzed, high-yield system for the oxidation of methane to methanol Science, vol. 259, Jan. 1993, pp. 340-343.

Periana et al Catalytic, oxidative condensation of $CH_4$ to $CH_3COOH$ in one step via CH activation Science, vol. 301, Aug. 2003, pp. 814-818.

Ryabov Mechanisms of intramolecular activation of C—H bonds in transition-metal complexes Chemical Reviews, vol. 90, No. 2, 1990, pp. 403-424.

Shu et al An $Fe^{10}_2O_2$ diamond core structure for the key intermediate Q of methane monooxygenase Science, vol. 275, No. 5299, Jan. 1997, pp. 515-518.

Solodov et al Distribution and geochemistry of contaminated subsurface waters in fissured volcanogenic bed rocks of the Lake Karachai Area, Chelyabinsk, Southern Urals Lawrence Berkeley Laboratory, University of California, USA, Jun. 1994, Report LBL-36780, UC-603.

Ogura et al: "Combined photochemical and electrochemical oxidation of methane", J. Electrochem. Soc., vol. 137, No. 2, 1990, pp. 500-503.

* cited by examiner

ELECTRO-CHEMICAL SENSOR

CROSS-REFERENCE TO RELATED APPLICATIONS

This application claims the benefits of priority from:
i) Application Number 0412926.8, entitled "ELECTRO-CHEMICAL SENSOR," filed in the United Kingdom on Jun. 9, 2004; and
ii) Application Number PCT/GB 2005/002237, entitled "ELECTRO-CHEMICAL SENSOR," filed under the PCT on Jun. 3, 2005;

All of which are commonly assigned to assignee of the present invention and hereby incorporated by reference in their entirety.

The invention relates to a chemical sensor tool for use in a wellbore and corresponding methods for analyzing of fluids produced from subterranean formations. More specifically, it relates to an electro-chemical sensor for methane analysis of effluents produced from subterranean formation.

BACKGROUND OF THE INVENTION

Analyzing samples representative of downhole fluids is an important aspect of determining the quality and economic value of a hydrocarbon formation.

Present day operations obtain an analysis of downhole fluids usually through wireline logging using a formation tester such as the MDT™ tool of Schlumberger Oilfield Services. However, more recently, it was suggested to analyze downhole fluids either through sensors permanently or quasi-permanently installed in a wellbore or through one or more sensors mounted on the drillstring. The latter method, where successfully implemented, has the advantage of obtaining data while drilling, whereas the former installation could provide additional value as part of a control system for wellbores and hydrocarbon production therefrom.

To obtain an estimate of the composition of downhole fluids, the MDT tools uses an optical probe to estimate the amount of hydrocarbons in the samples collected from the formation. Other sensors use resistivity measurements to discern various components of the formations fluids.

General downhole measurement tools for oilfield applications are known as such. Examples of such tools are found in the U.S. Pat. Nos. 6,023,340; 5,517,024; and 5,351,532 or in the International Patent Application WO 99/00575. An example of a probe for potentiometric measurements of ground water reservoirs is further published as: Solodov, I. N., Velichkin, V. I., Zotov, A. V. et al. "Distribution and Geochemistry of Contaminated Subsurface Waters in Fissured Volcanogenic Bed Rocks of the Lake Karachai Area, Chelyabinsk, Southern Urals" in: Lawrence Berkeley Laboratory Report 36780/UC-603 (1994b), RAC-6, Ca, USA.

If such devices were enabled to determine downhole trace amounts of light hydrocarbon molecules such as methane, they could offer an advance warning system for gas kicks, which is a major safety concern for drilling process. They could also provide valuable information regarding the location, distribution and composition of hydrocarbon reservoirs during logging operations.

The simple structure of methane and other gaseous, aliphatic hydrocarbons ($\leq C_5H_{12}$) means that only very limited potential reactions are available for these molecules. A particularly important reaction is their oxidative conversion into the corresponding alcohols. It is known that microbes existing in sub-surface reservoirs perform such conversion, in situ, via highly specific catalytic interactions involving embedded enzymes. A summary describing these microbes is found for example in: M. T. Madigan and B. L. Marrs, "Extremophiles", Sci. Am., 82-87 (1997).

The oxidative conversion chemistry of methane usually takes three major routes, two of which end up, ultimately, as $CO_2$ and $H_2O$ via one of the following sequences:

(1)

(2)

(3)

The most relevant and best understood reaction of methane so far is its partial oxidative conversion into methanol (reaction (1)), which is widely regarded as one of nature's greatest challenges to mankind, mainly due to the economic significance of the reaction product. Though thermodynamically feasible ($\Delta G^0 = -111.2$ kJ mol$^{-1}$), the reaction does not happen spontaneously to any observable extent under ambient conditions. Theoretical calculations show that neither elevated temperatures nor pressures result in substantial change in the free energy of the reaction.

At issue is the activation of the C—H bond, which is stronger in these gaseous hydrocarbons than in any other organic molecules. In nature, the activation process is enabled by the catalytic centre of the enzyme methane monooxygenase (MMO), in the presence of dioxygen, which, in turn, is activated by nicotinamide adenine dinucleotide hydride ion (NADH).

The catalytic centers in MMO that are responsible for the process of activating the C—H bond are, for soluble MMO, a diiron centre as described for example by L. Shu, J. C. Nesheim, K. Kauffmann, E. Munck, J. D. Lipscomb, L. Que, Jr., "An Fe$_2^{IV}$O$_2$ diamond core structure for the key intermediate Q of methane monooxygenase" Science, 275, 515-518 (1997) and for membrane-bound MMO, a tricopper cluster as described in H-H. T. Nguyen, A. K. Shiemke, S. J. Jacobs, B. J. Hales, M. E. Lidstrom and S. I. Chan, "The nature of the copper ions in the membranes containing the particulate methane monooxygenase from methylococcus capsulatus (Bath)", Biol. Chem., 269, 14995-15005 (1994).

Another known approach to methane activation is through an electro-chemical system which enables dioxygen to diffuse through a 130 µm thick silver membrane, which is controlled at a sufficiently negative potential to reduce the former into atomic oxygen, and react with methane on the other side. Sufficient dioxygen will then react with $CH_3$. radicals to form, via a complex chain reactions, methanol as against possible coupling dimer products. Details of this method are described by A. G. Anshits, A. N. Shigapov, S. N. Vereshchagin and V. N. Shevin, "C2 hydrocarbon formation from methane on silver membrane", Catal. Today, 6, 593-600 (1990)

An electro-chemical cell containing an iron-porphyrin deposited graphite cathode is known to convert light hydrocarbons into corresponding alcohols with considerable efficiency and described in: A. M. Khenin and A. E. Shilov, "Biomimetic alkane oxidation in the presence of iron complexes", New J. Chem., 13, 659-667 (1989).

Applications of a number of transition metal compounds as catalysts for the activation of methane partial oxidation are summarized in: A. D. Ryabov, "Mechanism of intermolecular activation of C—H bonds in transition metal complexes", Chem. Rev., 90, 403-424 (1990).

Periana et al. (J. H. Dygos, R. A. Periara, D. J. Taube, E. R. Evitt, D. G. Loffler, P. R. Wentrcek, Voss and T. Masuda, "A mercury-catalyzed, high-yield system for the oxidation of methane to methanol", Science, 259, 340-343 (1993))

reported a homogeneous catalytic system which led to a high yield of methanol from methane partial oxidation via methyl disulfate. The net reaction catalyzed by either mercury, thallium, palladium, platinum or gold ions is the oxidation of methane, via an electrophilic displacement mechanism, involving concentrated sulfuric acid to produce ~43% methyl disulfate. The subsequent hydrolysis resulted in methanol and simultaneous re-generation of the active form of the catalyst. The same group also most recently reported a one-step conversion of methane to acetic acid catalyzed by Pd in an acidic medium in: R. A. Periana, O. Mironov, D. Taube, G. Bhalla and C. J. Jones, "Catalytic, oxidative condensation of $CH_4$ to $CH_3COOH$ in one step via CH activation", *Science,* 301, 814-818 (2003).

It is also known that the C—H bond can also be activated by photolysis.

Various methane detection devices exist. In U.S. Pat. No. 4,282,487, a hydrocarbon detection system is described for the application of subsea oil and gas production. The system is based on a pair of inductive elements that are electrically coupled to the surrounding seawater. Displacement of conductive seawater by escaping hydrocarbons affects the interactions between the inductive elements, leading to a hydrocarbon-responsive output signal.

A wellsite alarm system designed to detect a sudden influx of hydrocarbon gases ("kicks") while drilling oil wells is described in U.S. Pat. No. 4,802,143. The system is based on a thermal conductivity sensor which responds to an abnormal amount of gas, presumably light hydrocarbons, in the mud, oil and gas mixture passing the sensor interface. Mounted with an acoustic impulse generator, this sensor operates at a predetermined threshold of gas concentration.

In the U.S. Pat. No. 5,351,532 there is described an in-hole probe to measure hydrocarbon concentrations in drilling fluids around the drill string. Ultra-violet irradiation is directed into a detection chamber, where the sensor apparatus determines the fluorescent energy radiating from ethanol-soluble, aromatic hydrocarbons. A mechanism is introduced to distinguish between the fluorescent signals originating from subsurface fluids and those caused by the diesel oil in drilling mud.

Whilst there are numerous examples of catalytic oxidation of methane, and a number of methods for detecting methane, it is an object of the present invention to provide a sensor for aliphatic hydrocarbons of low molecular weight. It is an object to make use of reaction processes for the purpose of monitoring hydrocarbon concentration, particularly for the purpose of determining methane concentration at subterranean locations. It is a further object of the present invention to provide downhole sensors and sensing methods for methane.

SUMMARY OF THE INVENTION

The invention proposes a sensor including a catalyst to convert hydrocarbons of low weight into reaction products and a detector to monitor the reaction progress or turnover in order to preferably derive from it a signal indicative of hydrocarbon concentration in the vicinity of the sensor. The reaction progress or turnover is preferably monitored using electro-chemical methods, i.e., through the measurement of currents and/or voltages, though other methods such as spectroscopic methods may also be suitable.

Preferably, the sensor takes advantage of the highly specific and effective interactions of a catalyzed reaction, more preferably between either the soluble enzyme methane monooxygenase (MMO), a compound that activates essentially the same reaction as MMO, or between a selection of transition metal compounds and methane.

Either immobilized onto the surface of a conducting substrate, or embedded in a porous substrate or as part of a liquid solution, a redox active centre of the enzyme, or the selected metal compound, is capable of initiating the partial oxidation of methane into methanol. The resultant oxidation current, the magnitude of which is proportional to the concentration of methane, offers a preferred quantitative determination of the target molecule. Preferably assembled as a rugged, no-moving-parts device, such a sensor can be readily integrated into a drill string, production logging tool and open hole formation tester tool such as the MDT™ tool of Schlumberger.

These and other features of the invention, preferred embodiments and variants thereof, possible applications and advantages will become appreciated and understood by those skilled in the art from the following detailed description, appended drawings and claims.

DETAILED DESCRIPTION OF THE INVENTION

In a first example an electrochemical device is used with a synthetic compound that mimics the structure, and hence the function, of the redox active center of methane monooxygenase (MMO) as the catalyst. In the present example, the synthetic compound is a diiron $Fe^{IV}_2O_2$.

Figure 1:
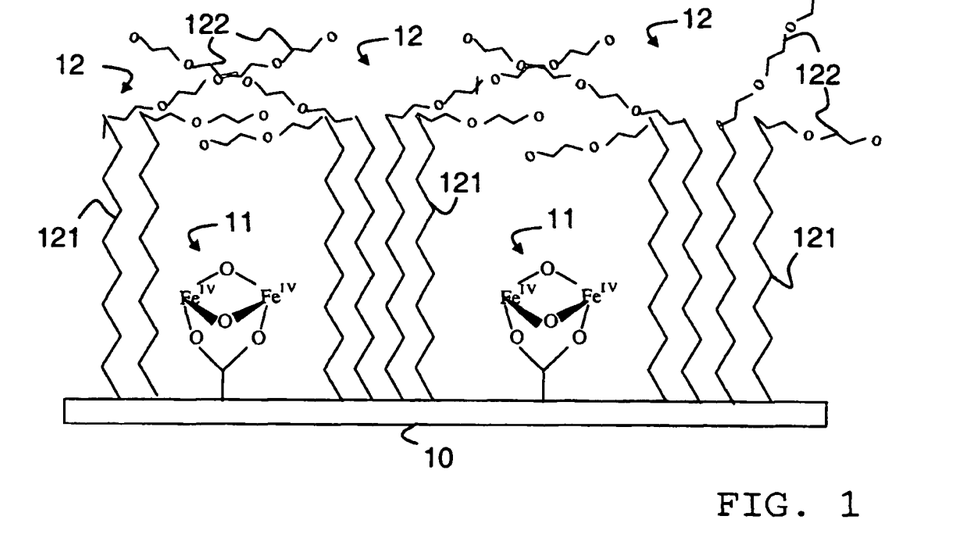
FIG. 1 illustrates a surface section of a sensor in accordance with an example of the invention.

As schematically illustrated in FIG. 1, the diiron is immobilized through a covalent bond to a conducting surface or substrate 10. The substrate is carbon, but other materials such as steel or titanium dioxide are also suitable. The bonding can be achieved through known methods such as the reduction of an amine or silanisation.

In its immobilized state, the diiron $Fe^{IV}_2O_2$ complex 11 in a diamond core structure as described by Shu et al above remain electro-chemically active. The distance between the diiron complex 11, with an Fe—Fe distance of about 0.25 nm, and the surface 10 can be readily controlled to limit the distance that electrons effectively travel to about 1 nm, thus ensuring the rapid electron transfer process of the redox center.

In the example shown the individual catalytic centers 11 are surrounded by aliphatic molecules 12, which form a protection membrane for the iron complex. The membrane is one way of protecting the centers from direct exposure to well bore fluids. It consists of two parts: The lower part 121 is formed by relatively rigid, saturated hydrocarbon chains of up to 18 C atoms in the backbone structure. The upper part 122 includes more flexible polyethylene glycol chains ((—CH$_2$CH$_2$O—)$_n$, n=5-10).

In operation, the diiron compound is maintained in its oxidized form under a controlled electrode potential. The methane is oxidized as it diffuses through the protection barrier 12.

As an alternative to the diiron catalysts, other suitable catalysts and reactions can be used. For example Fe$_2$(SO$_4$)$_3$ as acidic buffer solution in the presence of a catalyst, either Pd, or Ag-loaded Pd or Pt, selectively converts methane into methanol through an electro-chemical process.

As an alternative to the covalent bonding described in FIG. 1, the catalyst may be immobilized by blending it with an appropriate conducting sphere (e.g. carbon, or boroncarbide, or metallic species such as gold, silver or platinum, in either micrometric or nanometric scales) and disperse the blend into an epoxy matrix. This alternative is described in greater detail in the co-owned published international patent application WO 2004/011929. As a further alternative, the catalyst may be part of a slurry of ionic liquids at room temperature following a process described for example by T. Fukushima, A. Kosaka, Y. Ishimura, T. Yamamoto, T. Takigawa, N. Ishii, T. Aida in: Science, 300 (2003), 2072-2074.

Figure 2:
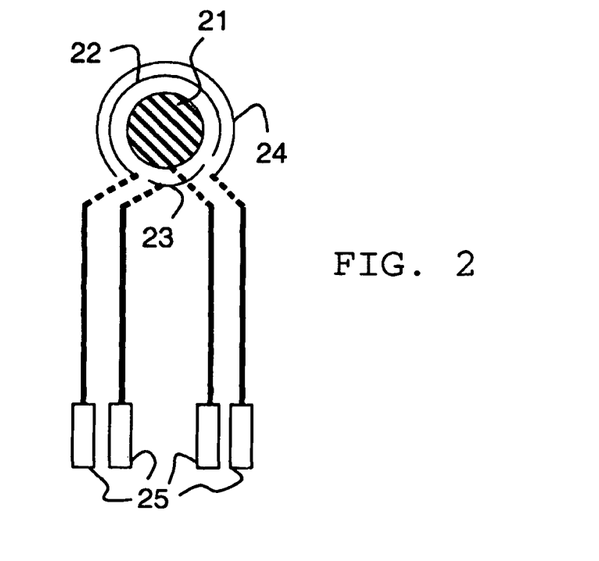
FIG. 2 is a schematic layout of electrodes of a sensor in accordance with an example of the invention.

The sensor of the above example is configured according to FIG. 2, where a catalyst coated central disk 21 is surrounded by a ring counter electrode 22 and a (smaller) ring reference electrode 23. The working electrode can be made from any of the above substrate material, including metal (steel, gold or platinum), titanium dioxide, carbon, or diamond doped with either boron or nitrogen.

An outer-ring electrode 24 maintained at a controlled potential is used to generate a localized and, mainly, upwards gas bubble streams via the hydrolysis of water. The stream prevents or reduces fouling of the electrode active surface 21. In addition to its cleaning function, this process offers a supply of in-situ produced dioxygen. As oxygen is required by the reaction, the additional oxygen stream may augment or replace oxygen contained in the drilling mud. Contact pads 25 provide lead-outs to electronic circuits (not shown) to control and measure the currents and voltages required for or generated by the redox reaction. After calibration, the current is readily convertible into a reading of the concentration of methane in the vicinity of the sensor.

Where alternatives to the covalent bonding described in FIG. 1 are employed, the electrodes may be designed similar to the sensor in the co-owned published international patent application WO 2004/011929 using a porous block of material with electrodes molding in.

Figure 3:
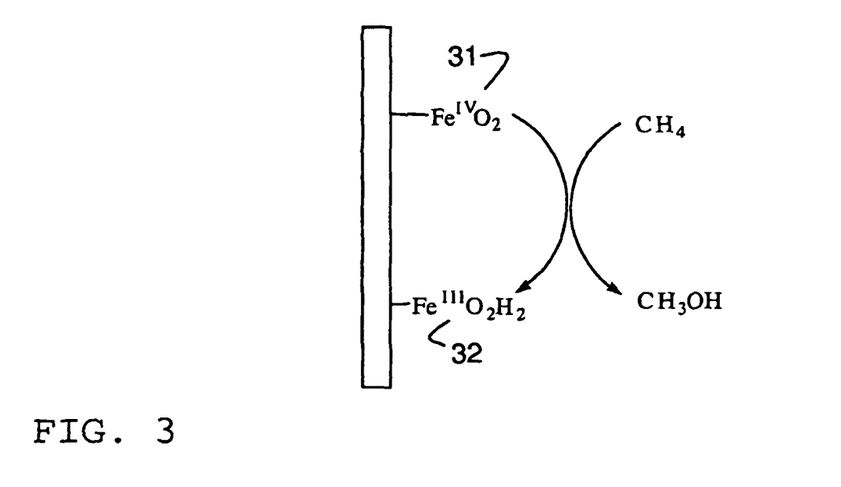
FIG. 3 illustrates an operation of a sensor in accordance with an example of the invention.
Figure 4:
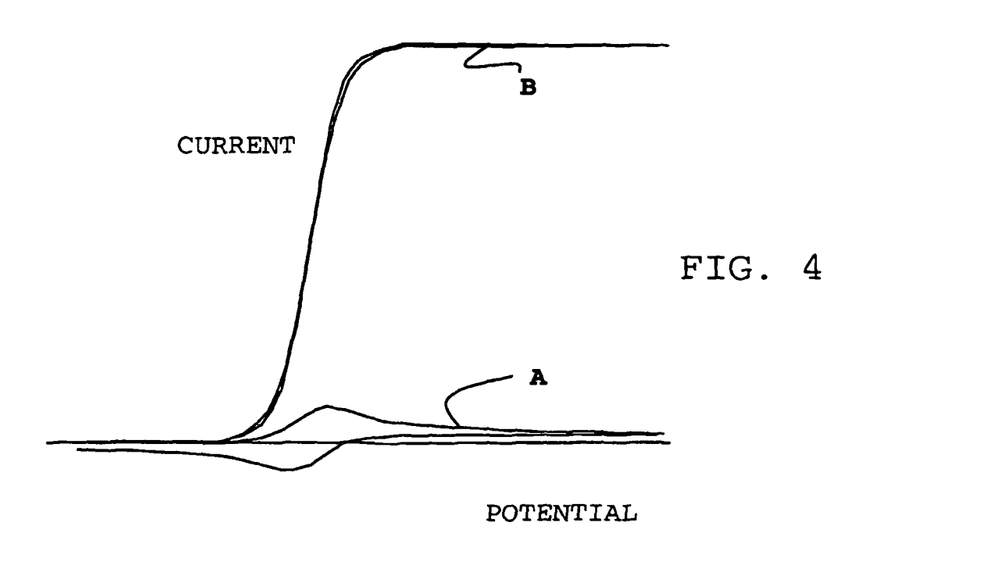
FIG. 4 is a plot of current-voltage curves without and with methane present.

The redox process, itself, as it occurs at the active centers of the sensor is illustrated in FIG. 3. A reduced form 32 of the diiron compound 31, produced by the homogeneous interaction with methane, is immediately converted back to the oxidised form by the heterogeneous electrode reaction. Since the reaction rate of the homogeneous interaction is over 1000 fold faster than that of the heterogeneous turnover of the catalyst, there is a significant enhancement of the current on the encounter of the target methane molecule. The increase is illustrated in FIG. 4 showing the sigmoid-shaped, steady state (Curve B) of the oxidation current of the catalyst and the peak-shaped, transient (Curve A) of the heterogenous turnover. The magnitude of the resultant oxidation current of the reduced form of the diiron compound is proportional to the concentration of methane, and hence offers a quantitative measure for the target molecule.

As an alternative to the measurement of the currents flowing, the reaction process may also be monitored using optical methods such as laser spectroscopy, which probes the electron transfer kinetics involved in the reaction chain.

Figure 5:
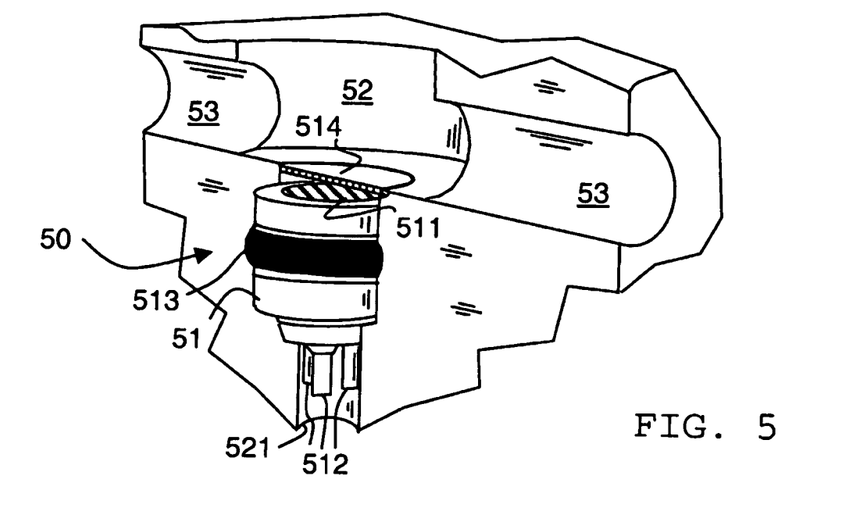
FIG. 5 is a perspective view, partially cut-away, of a sensor in accordance with an example of the present invention in a downhole tool.

A sensor assembly 50 using the electrode configuration as shown in FIG. 2, can be coupled to a flowline 53 in a manner described in FIG. 5. The body 51 of the sensor is fixed into the end section of an opening 52. The body carries the electrode surface 511 and contacts 512 that provide connection points to voltage supply and measurement through a small channel 521 at the bottom of the opening 52. A sealing ring 513 protects the contact points and electronics from the wellbore fluid that passes under operation conditions through the sample channel 53. A membrane 514 protects the electrode 511 from direct contact with the fluid passing through the flowline 53.

Methane dissolved in the fluid permeates to the functionalised surface 511 of the electrode through the gas permeable membrane 514. Depending on the environment and the electrode preparation, the membrane 514 may be replaced by or used in combination with the molecular membrane as shown in FIG. 1 or with a microporous epoxy matrix embedding the catalysts.

When using catalyst in a slurry or buffer solution as described in the alternatives above, the solution or slurry can be placed behind the gas permeable membrane 514 that separates the multiphase flow stream from the electro-chemical cell in which the measurement is taking place.

A distinctive advantage of the sensor is that it is capable of detecting very low concentration level of methane in the range of ppb and hence can offer for example advance warning of any potential methane leaks or gas kicks.

It is worth noting that MMO, and hence its catalytic center, does not exhibit a strict specificity to methane. Instead it activates, with increasingly lower sensitivity, the light aliphatic hydrocarbons up to length of 5 C atoms (pentane) covering a whole range of gaseous species. But since methane is present in an overwhelming concentration compared to those gases and also has the fastest velocity, the detection approach of this invention will ensure a highly effective specificity towards methane in all downhole applications.

On the other hand, the specificity range can be exploited using either the above described examples of redox centers or other enzyme redox centers to target hydrocarbons starting from increasingly higher molecular weight, i.e., C2, C3, etc. Essential information could thus be gained as to the composition and distribution of oil reservoir, and the permeability of the rock structure.

The sensors of the present invention such as described in the example of FIG. 5 or alternatives thereof can be used in a variety of measurements, some of which are described below in greater detail.

In the following various possible downhole applications of the novel sensor are described making reference to FIGS. 6-8.

Figure 6:
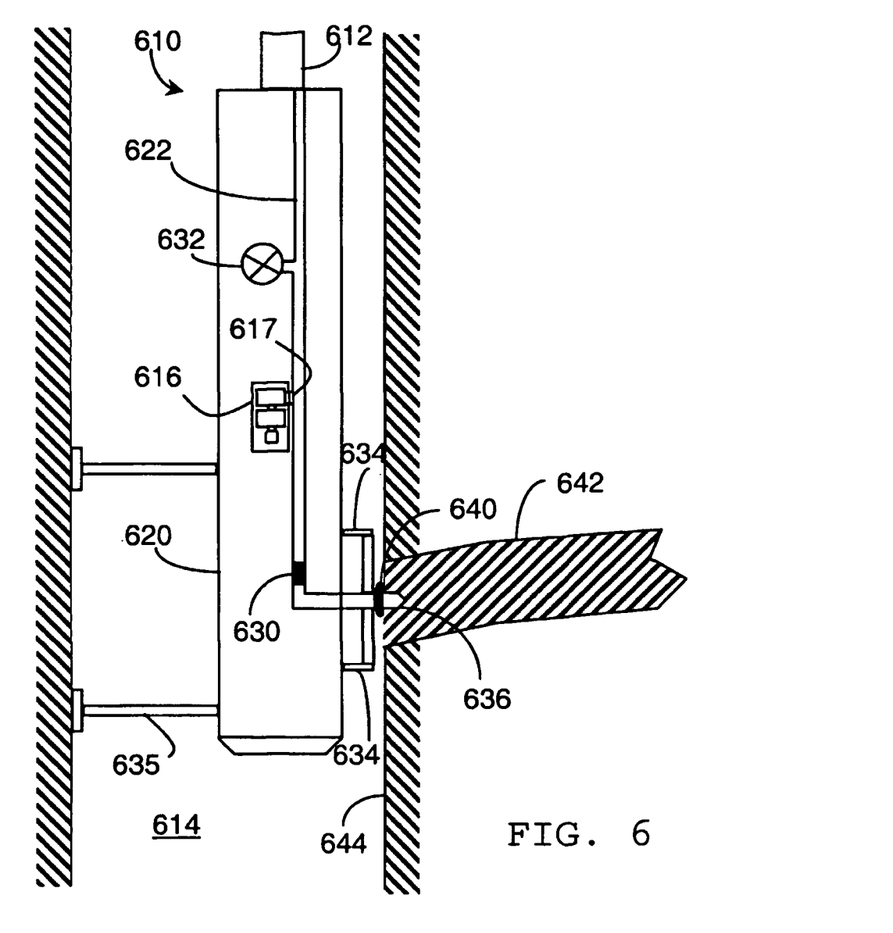
FIG. 6 illustrates an example of a sensor in accordance with the invention as part of a wireline formation testing apparatus in a wellbore.

In FIG. 6, there is shown a formation testing apparatus 610 held on a wireline 612 within a wellbore 614. The apparatus 610 is a well-known modular dynamic tester (MDT, Mark of Schlumberger) as described in the co-owned U.S. Pat. No. 3,859,851 to Urbanosky U.S. Pat. No. 3,780,575 to Urbanosky and Pat. No. 4,994,671 to Safinya et al., with this known tester being modified by introduction of a methane sensor 616 as described in detail above (FIG. 5). The modular dynamics tester comprises body 620 approximately 30 m long and containing a main flowline bus or conduit 622. The methane sensor 616 communicates with the flowline 622 via opening 617. In addition to the novel methane sensor 616, the testing apparatus comprises an optical fluid analyser 630 within the lower part of the flowline 622. The flow through the flowline 622 is driven by means of a pump 632 located towards the upper end of the flowline 622. Hydraulic arms 634 and counterarms 635 are attached external to the body 620 and carry a sample probe tip 636 for sampling fluid. The base of the probing tip 636 is isolated from the wellbore 614 by an o-ring 640, or other sealing devices, e.g., packers.

Before completion of a well, the modular dynamics tester is lowered into the well on the wireline 612. After reaching a target depth, i.e., the layer 642 of the formation which is to be sampled, the hydraulic arms 634 are extended to engage the sample probe tip 636 with the formation. The o-ring 640 at the base of the sample probe 636 forms a seal between the side of the wellbore 644 and the formation 642 into which the probe 636 is inserted and prevents the sample probe 636 from acquiring fluid directly from the borehole 614.

Once the sample probe 636 is inserted into the formation 642, an electrical signal is passed down the wireline 612 from the surface so as to start the pump 632 and the sensor systems 616 and 630 to begin sampling of a sample of fluid from the formation 642. The sensor 616 is adapted to measure the concentration of methane of the formation effluent.

A bottle (not shown) within the MDT tool may be filled initially with a calibration solution to ensure in-situ (downhole) calibration of sensors. The MDT module may also contain a tank with a greater volume of calibration solution and/or of cleaning solution which may periodically be pumped through the sensor volume for cleaning and re-calibration purposes.

A further possible application of the novel sensor and separation system is in the field of measurement-while-drilling (MWD). The principle of MWD measurements is known and disclosed in a vast amount of literature, including for example U.S. Pat. No. 5,445,228, entitled "Method and apparatus for formation sampling during the drilling of a hydrocarbon well".

Figure 7:
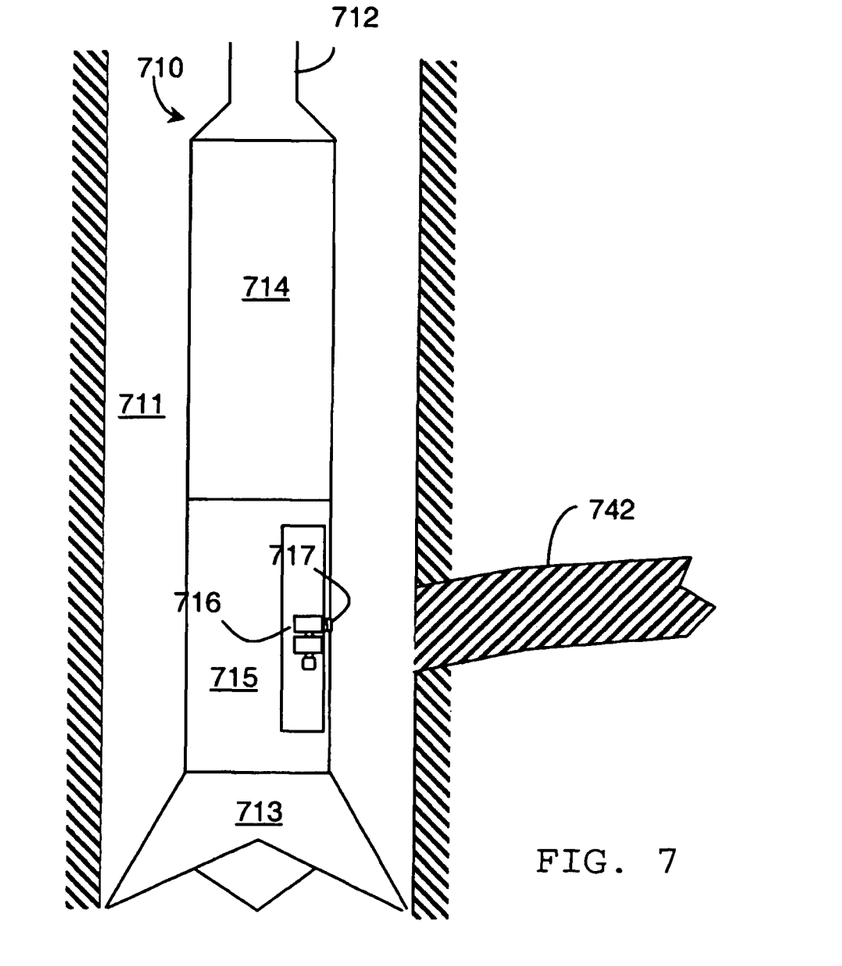
FIG. 7 shows a wellbore and the lower part of a drill string including the bottom-hole-assembly, with a sensor in accordance with the invention.

In FIG. 7, there is shown a wellbore 711 and the lower part of a drill string 712 including the bottom-hole-assembly (BHA) 710. The BHA carries at its apex the drill bit 713. It includes further drill collars that are used to mount additional equipment such as a telemetry sub 714 and a sensor sub 715. The telemetry sub provides a telemetry link to the surface, for example via mud-pulse telemetry. The sensor sub includes a novel methane sensor 716 as described above. The sensor unit 716 collects fluids from the wellbore and hence from oil-bearing layers such as layer 742 via a small recess 717 protected from debris and other particles by a metal mesh.

During drilling operation wellbore fluid enters the recess 717 and is subsequently analyzed using sensor unit 716. The results are transmitted from the data acquisition unit to the telemetry unit 714, converted into telemetry signals and transmitted to the surface.

Figure 8:
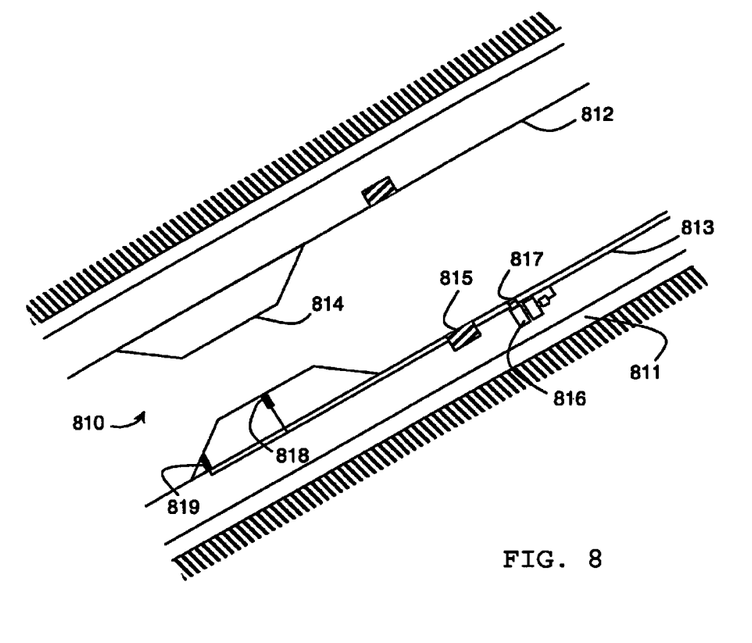
FIG. 8 shows a sensor located downstream of a venturi-type flowmeter in accordance with the invention.

A third application is illustrated in FIG. 8. It shows a Venturi-type flowmeter 810, as well known in the industry and described for example in the U.S. Pat. No. 5,736,650. Mounted on production tubing or casing 812, the flowmeter is installed at a location within the well 811 with a wired connection 813 to the surface following known procedures as disclosed for example in the U.S. Pat. No. 5,829,520.

The flowmeter consists essentially of a constriction or throat 814 and two pressure taps 818, 819 located conventionally at the entrance and the position of maximum constriction, respectively.

Usually the Venturi flowmeter is combined with a densiometer 815 located further up- or downstream.

The novel methane sensor 816 is preferably located downstream from the Venturi to take advantage of the mixing effect the Venturi has on the flow. A recess 817 protected by a metal mesh provides an inlet to the unit.

During production wellbore fluid enters the recess 817 and is subsequently analyzed using sensor unit 816. The results are transmitted from the data acquisition unit to the surface via wires 813.

A sensor in accordance with the present invention will also be applicable for the detection of methane gas leaking in transportation and other industrial and domestic environments.

A particular example is the possible exploration of the seafloor for reserves of gashydrates. In addition, it can be used in the application for advance warning and reservoir mapping in coal bed methane mining.

Various embodiments and applications of the invention have been described. The descriptions are intended to be illustrative of the present invention. It will be apparent to those skilled in the art that modifications may be made to the invention as described without departing from the scope of the claims set out below.

The invention claimed is:

1. An electro-chemical sensor for measuring methane in situ, comprising:
    a first electrode coupled with a plurality of activation centers, the plurality of activation centers comprising a catalyst that at least partially oxidizes methane under standard conditions for a redox reaction producing reaction products including methanol, wherein the first electrode is in discrete contact with the reaction products and the catalyst comprises one of an iron, copper or transition metal compound, and wherein the plurality of activation center comprises the catalyst surrounded by a membrane comprising aliphatic molecules having a lower end comprising saturated hydrocarbon chains of up to 18 carbon atoms in the backbone structure and an upper end comprising polyethylene glycol chains and the lower end of the aliphatic molecules are coupled to the first electrode;
    a second electrode in discrete contact with the reaction products;
    a third electrode configured to be held at a fixed potential and generate a stream of dioxygen bubbles by hydrolyzing water; and
    an electronic circuit electrically coupled with the first and the second electrodes and configured to measure an oxidation current resulting from the partial oxidation of the methane into methanol, wherein a magnitude of the oxidation current is proportional to a concentration of the methane.

2. The electro-chemical sensor of claim 1, wherein the first electrode comprises a sensing electrode and the second electrode comprises a counter electrode.

3. The electro-chemical sensor of claim 2, further comprising a reference electrode in discrete contact with the reaction products.

4. The electro-chemical sensor of claim 1, wherein the catalyst is immobilized on a surface of the first electrode.

5. The electro-chemical sensor of claim 1, wherein the catalyst is immobilized through covalent chemical bonds on a surface of the first electrode.

6. The electro-chemical sensor of claim 1, wherein the catalyst is selected from a group comprising, diiron, $Fe_2(SO_4)_3$ and tri-copper compounds.

7. A downhole tool for measuring characteristic parameters of wellbore effluents, comprising the electro-chemical sensor in accordance with claim 1.

8. The downhole tool of claim 7, wherein the electrochemical sensor is mounted on a downhole fluid sampling tool.

9. The downhole tool of claim 7, wherein the electrochemical sensor is mounted onto a permanently installed part of a wellbore.

10. The downhole tool of claim 7, wherein the electrochemical sensor is mounted onto a drill string.

* * * * *